(12) United States Patent
Gregory

(10) Patent No.: US 6,632,450 B1
(45) Date of Patent: Oct. 14, 2003

(54) ADHERABLE BIOMATERIAL PATCHES AND METHODS FOR PRODUCING AND FOR USING SAME

(75) Inventor: Kenton W. Gregory, Portland, OR (US)

(73) Assignees: Kenton Gregory, Portland, OR (US); Providence Health System-Oregon, Seattle, WA (US)

(*) Notice: Subject to any disclaimer, the term of this patent is extended or adjusted under 35 U.S.C. 154(b) by 0 days.

(21) Appl. No.: 09/859,737

(22) Filed: May 16, 2001

Related U.S. Application Data

(60) Provisional application No. 60/204,916, filed on May 16, 2000.

(51) Int. Cl.[7] .......................... A61F 13/00; A61F 2/00; A61K 9/70; A61L 15/00
(52) U.S. Cl. ................. 424/443; 424/444; 424/445; 424/446; 424/447; 424/448; 424/449; 424/422; 424/423
(58) Field of Search ................. 606/214, 213; 424/422, 423

(56) References Cited

U.S. PATENT DOCUMENTS

| | | | |
|---|---|---|---|
| 5,583,114 A | * | 12/1996 | Barrows et al. ......... 424/179.1 |
| 5,989,244 A | | 11/1999 | Gregory |
| 5,990,379 A | | 11/1999 | Gregory |
| 6,087,552 A | | 7/2000 | Gregory |
| 6,110,212 A | | 8/2000 | Gregory |
| 6,299,631 B1 | * | 10/2001 | Shalaby ..................... 606/214 |
| 6,372,228 B1 | | 4/2002 | Gregory |

OTHER PUBLICATIONS

Debra Bedell–Hogan, Philip Trackman, William Abrams, Joel Rosenbloom and Herbert Kagan, Oxidation, Cross–Linking, and Insolubilization of Recombinant Tropoelastin by Purified Lysyl Oxidase, (Journal of Biological Chemistry, vol. 268, No 14, Issue of May 15, pp. 10345–10350, 1993.

* cited by examiner

Primary Examiner—Thurman K. Page
Assistant Examiner—Isis Ghali
(74) Attorney, Agent, or Firm—Marger Johnson & McCollom, P.C.

(57) ABSTRACT

This invention relates to a method for producing an adherable biomaterial patch. The subject patch is capable of being joined onto a tissue substrate. The invention is also directed to the patch per se, and to a method for producing the adherable biomaterial patch which is joined onto a tissue substrate. A preferred patch can even function in a highly acidic environment. The method of the present invention comprises providing a biomaterial patch consisting essentially of elastin or an elastin-based biomaterial having at least one outer surface. Next, at least one outer surface of the biomaterial patch is treated with a selected cyanoacrylate adhesive to produce a adherable biomaterial patch.

51 Claims, 7 Drawing Sheets

ADHERABLE BIOMATERIAL PATCHES AND METHODS FOR PRODUCING AND FOR USING SAME

RELATED APPLICATION

This application claims priority from Provisional Application Serial No. 60/204,916 filed on May 16, 2000.

This invention was made with Government support under Grant Nos. DAMD17-96-1-6006 and DAMD17-98-1-8654 awarded by U.S. Army Medical Research Acquisition Activity. The U.S. Government has certain rights in the invention.

BACKGROUND OF THE INVENTION

The present invention relates to adherable biomaterial patches, to methods of producing the patches, and more particularly to methods of using such patches, particularly in tissue repair.

Elastic fibers are responsible for certain elastic properties of tissues such as skin and lung, as well as arteries, and are composed of two morphologically distinct components, elastin and microfibrils. Microfibrils make up the quantitatively smaller component of the fibers and play an important role in elastic fiber structure and assembly.

The most abundant component of elastic fibers is elastin. The entropy of relaxation of elastin is responsible for the rubber-like elasticity of elastic fibers. Elastin is an extracellular matrix protein that is ubiquitous in mammals. Elastin is found, for example, in skin, blood vessels, and tissues of the lung where it imparts strength, elasticity and flexibility. In addition, elastin, which is prevalent in the internal elastic lamina (IEL) and external elastic lamina (EEL) of the normal artery, may inhibit the migration of smooth muscle cells into the intima.

In vertebrates elastin is formed through the secretion and crosslinking of tropoelastin, the 72-kDa biosynthetic precursor to elastin. This is discussed, for example, in an article entitled "Oxidation, Cross-linking, and Insolubilization of Recombinant Crosslinked Tropoelastin by Purified Lysyl Oxidase" by Bedell-Hogan, et al in the Journal of Biological Chemistry, Vol. 268, No. 14, on pages 10345–10350 (1993).

As described in certain prior issued patents and in co-pending patent applications of one of the co-inventors herein, namely, U.S. Pat. No. 5,989,244 issued on Nov. 23, 1999, U.S. Pat. No. 5,990,379 issued on Nov. 23, 1999, U.S. Pat. No. 6,087,552 issued on Jul. 11, 2000 and U.S. Pat. No. 6,110,212 issued on Aug. 29, 2000, U.S. Ser. No. 09/000,604 filed on Dec. 30, 1997 all of which are incorporated herein by reference, elastin and elastin-based biomaterials, can be used in a number of medical applications.

These elastin and elastin-based biomaterials are typically sutured or fused to the tissue. Fusing is generally accomplished employing an energy absorbing material, and irradiating the energy absorbing material with light energy in a predetermined wavelength range with an intensity sufficient to facilitate the fusing operation.

Major life threatening injuries to areas of the human body, such as the gastrointestinal system, the pulmonary system, and the vascular system, require extensive surgical repairs, which may result in significant tissue loss, leading to morbidity and mortality. Certain areas of the body in particular, such as the gastrointestinal system and the lungs, require repairs which take into account the need for both flexibility and strength. Furthermore, the harsh environment of the gastrointestinal system, such as in the duodenum, is formed of acidic chyme from the stomach, pancreatic alkaline secretions, and a multitude of hormones and enzymes including proteases and lipases. The duodenum has the most severe conditions within the gastrointestinal system with pH extremes and digestive enzymes. Current treatments for injuries in these areas involves complex and lengthy surgeries with prolonged post-surgical drainage and delayed feeding.

Suturing and fusing of a patch onto a tissue substrate such as the lungs or in a highly acidic environment, such as the gastrointestinal system, the pulmonary system, and the vascular system, is both difficult and time consuming to complete. It is also a problem to maintain the patch in place for extended periods of time without incurring incidences of infection in the area which the repair has taken place. Suturing patches into the lung creates air leaks in the lung which can lead to lung collapse. Furthermore, laser fusion of patches can lead to unwanted thermal injury to the underlying lung tissue. Also, laser fusion of patches for the gastrointestinal system is typically not resistant to GI enzymes.

Adhesives for joining materials to human tissue are known. In order to be an acceptable in vivo adhesive for use in conjunction with lung or gastrointestinal applications, it must be non-toxic, non-inflamatory, sterilizable, biodegradable, flexible and exhibit certain strength properties. Prior art adhesives do not possess the above-described properties required for use in vivo in applications such as in the lungs or gastrointestinal system or leak sufficient resistance to acids and enzymes in during tissue substrate repair.

SUMMARY OF THE INVENTION

A biomaterial patch including a selected cyanoacrylate adhesive can effectively seal an injury of the gastrointestinal system, the pulmonary system, or the vascular system, thereby preventing leakage from that organ. The biomaterial patch, which consists essentially of elasin, or an elastin biomaterial, may serve as an effective physical and chemical barrier for repair of injuries which occur in the human body, particularly in portions of the body which can exhibit highly acidic environments. Typically, the biomaterial patch-tissue seal formed is water-tight and air-tight in nature. The biomaterial patches of the present invention meet the above-described use criteria, namely, they are non-toxic, non-inflamatory, sterilizable, biodegradable, flexible and exhibit excellent strength properties. The patch-tissue seal can be formed within minutes so that the repair procedure can be performed quickly and maintained in place during the healing process.

The subject biomaterial patch is relatively chemically inert. Therefore, it provides sufficient resistance to degradation by, if need be, highly acidic contents, to allow healing. By using a tissue adhesive as opposed to traditional sutures, such as a modified cyanoacrylate-based adhesive, the biomaterial patch can be quickly applied. Then, the patch of the present invention can typically achieve a fluid-tight or air-tight seal and thereby decrease the incidence of infection, air or fluid leaks that may be deleterious to haling and tissue health.

Other preferred properties of the patch are that it is sterilizable, minimally immunogenic, and resistant to digestive enzymes and acids. This combination of a biomaterial patch, and a tissue adhesive which can join the patch onto the tissue for a period of time sufficient to facilitate healing of the damaged tissue, can provide an innovative approach to repair of these injuries by decreasing post-operative complications, thereby increasing chances of full functional recovery.

This invention relates to a method for producing an adherable biomaterial patch. The subject patch is capable of being joined onto a tissue substrate. The invention is also directed to the patch per se, and to a method for producing the adherable biomaterial patch which is joined onto a tissue substrate. A preferred patch can even function in a highly acidic environment.

The method of the present invention comprises providing a biomaterial patch consisting essentially of elastin or an elastin-based biomaterial having at least one outer surface. Next, at least one outer surface of the biomaterial patch is treated with a selected cyanoacrylate adhesive to produce a adherable biomaterial patch.

The adherable biomaterial patch exhibits a Minimum Hold Time when joined onto the tissue substrate, typically a live tissue substrate, preferably in a highly acidic environment. This Minimum Hold Time is typically at least about 48 hours, preferably at least about 72 hours, more preferably at least about 96 hours, and most preferably at least about 7 days.

The biomaterial patch is typically unilaminar or bilaminar in nature, preferably bilaminar, where additional patch strength is desired. It also preferably forms a substantially water-tight seal, as well as a substantially air-tight seal, when joined onto a tissue substrate.

The method of the present invention can be conducted in an environment, when the adherable biomaterial patch joined onto the tissue substrate, which attains a highly acidic level. More specifically, the pH attained during the period in which the adherable biomaterial patch joined onto the tissue substrate is typically up to about 4.5, more typically up to about 5.0, and most typically up to about 6.0. Moreover, the tissue substrate can be the gastrointestinal system, or a portion thereof, such as the duedenum.

The adherable biomaterial patch has a Shear Strength (24 hour) which is preferably at least about 10 kPa, more preferably at least about 12 kPa, and most preferably at least about 15 kPa. The adherable biomaterial patch can have a Shear Strength (7 day) which is preferably at least about 10 kPa, more preferably at least about 12 kPa, and most preferably at least about 15 kPa.

Shear strength for the subject adherable biomaterial patch is measured using a Chatillon V1000 Mechanical Tester, as follows:

1. Prepare the sample by cutting it into two halves lengthwise.
2. Then overlap one end of the first half with one end of the second half. Ensuring that the two pieces are attached only within on the overlapped region as shown in the figure below. If gluing the 2 pieces, use 30 µl of glue.
3. Measure the area of overlap of the two pieces using a calipers and record.
4. Choose a load cell and calibrate.
5. Using the load cell, zero the position and tare the force. Make sure that the grips are touching
6. Attach the sample to the grips, and move the upper grip until the sample is not sagging, is centered and aligned. At this point, make sure that the force is still 0±0.025 g.
7. Acquire data at a 20 Hz frequency, 1 mm/sec stretch rate. Make sure that the tester is actually set to exert 100% of the load cell being used.
8. Open the data in Excel 98. Use the macro, GlueTestStart. Enter the measured overlap are (mm2) in cell C2.
9. Shear Stress (kPa) is calculated using Overlap area (length×width) for each sample.

The adherable biomaterial patch has a Flexibility which is preferably at least about 100 kPa, more preferably at least about 125 kPa, and most preferably at least about 150 kPa.

Flexibility for the subject adherable biomaterial patch is measured, using a Chatillon V1000 Mechanical Tester, as follows:

1. Measure the surface area of the sample using a calipers and record.
2. Choose a load cell and calibrate.
3. Using the load cell, zero the position and tare the force. Make sure that the grips are touching.
4. Attach the sample to the grips, and move the upper grip until the sample is not sagging, is centered and aligned. At this point, make sure that the force is still 00±0.025 g.
5. Acquire data at a 20 Hz frequency, 1 mm/sec stretch rate, and fix the pull distance to about 2000 µm (ensure sample does not break). Make sure that the tester is actually set to exert 100% of the load cell being used.
6. This initial pull of the sample gives its elastic modulus, which serves as a comparison against the combined modulus of the sample and the adhesive.
7. Coat one surface of the sample with the tissue adhesive 20±5 µl and allow the adhesive to dry. The drying sample should be placed in a moist, though not wet, environment to keep the elastin hydrated.
8. Once the adhesive is dry, measure its thickness as well as the sample width using calipers.
9. Repeat steps 4, 5 and 6. Make sure the pull distance is set to break the, sample.
10. Open the data for each of the two files, sample's pre-stretch and the adhesive-coated sample, in Excel 98. Use the macro GlueTestStart. Enter the measured adhesive area (sample width (mm)×thickness (mm) in cell C2.
11. Elastic modulus (kPa) for both the pre-stretched sample, and the adhesive-coated sample is calculated as the slope of the linear portion of the curve.

The adherable biomaterial patch generally has cure rate which allows the user to join same in place in after the passage of a relatively sort period of time. Thus, the adherable biomaterial patch has a Minimum Cure Time of at not more than about 5 Minutes, preferably not more than about 4 Minutes, more preferably not more than about 3 Minutes.

The adhesive of this invention is typically a cyanoacrylate adhesive, preferably an alkoxyalkyl cyanoacrylate, more preferably a methoxyalkyl cyanoacrylate, and most preferably methoxypropyl cyanoacrylate. In a particularly preferred form of this invention, the cyanoacrylate adhesive further can include an additive which is typically a polymeric material. For example, an absorbable cyanoacrylate-based tissue adhesive, developed and manufactured by PolyMed, Inc. of Anderson, S.C., can be used to adhere the patch of this invention to the tissue. A preferred PolyMed adhesive which can be employed is denoted as GF-62 which comprises 95% by weight of methoxypropyl cyanoacrylate and 5% by weight of a solid miscible polymeric additive comprising a copolymer of caprolactone and glycolide. Another preferred PolyMed adhesive is GF-89B which comprises 97% by weight of methoxypropyl cyanoacrylate and 3% by weight of a solid miscible polymeric additive comprising VG3. The additive for the cyanoacrylate adhesive is typically provided in an amount up to about 5% by weight, preferably the amount of these additives is up to about 10% by weight, more preferably up to about 15% by weight, and most preferably up to about 20% by weight, based on the total weight of the cyanoacrylate and the additive, based on the total weight of the adhesive.

Further objects and advantages of the invention will be clear from the description that follows.

DETAILED DESCRIPTION OF A PREFERRED EMBODIMENT

Figure 1:
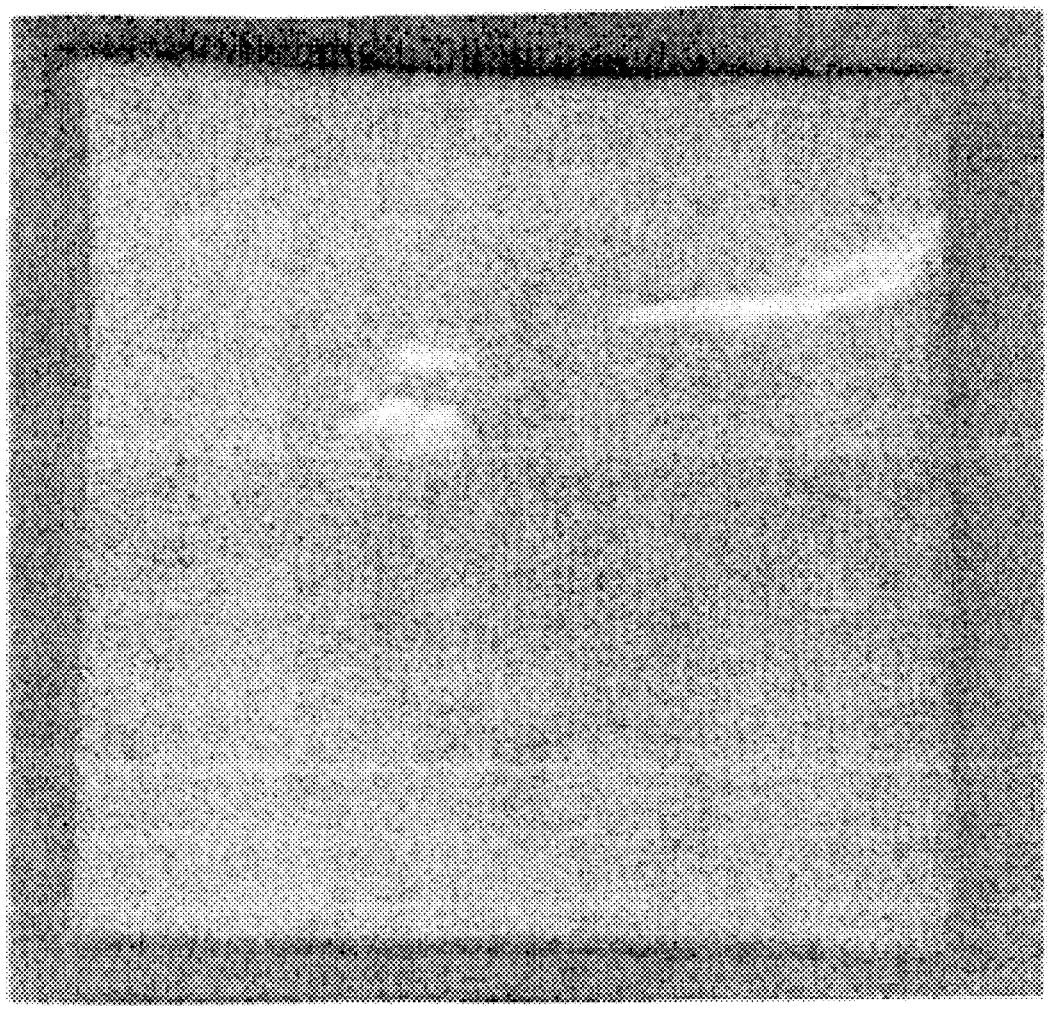
FIG. 1: Bilaminar elastin patch.

Elastin-based biomaterials suitable for use in the present invention can be prepared, for example, from elastin (e.g. from bovine nuchal ligament), as described by Rabaud et al (U.S. Pat. No. 5,223,420). (See also Aprahamian et al, J. Biomed. Mat. Res. 21:965 (1987); Rabaud et al, Thromb. Res. 43:205 (1986); Martin, Biomaterials 9:519 (1988).) A further type of elastin-based biomaterial suitable for use in the present invention is prepared as described by Urry et al (see, for example, U.S. Pat. Nos. 4,132,746 and 4,500,700) (See also U.S. Pat. Nos. 4,187,852, 4,589,882, 4,693,718, 4,783,523, 4,870,055, 5,064,430, 5,336,256). Elastin matrixes resulting from digestion of elastin-containing tissues (eg arteries) can also be used. Digestion results in the removal of cells, proteins and fats but maintenance of the intact elastin matrix. The biomaterial used will depend on the particular application.

The biomaterials of the invention prepared, for example, from soluble elastin (see Rabaud et al above) can be molded so as to render it a suitable size and shape for any specific purpose. Molded biomaterial can be prepared as follows. Elastin (eg soluble elastin (MW 12–32,000 daltons) is washed and swollen in buffer. The mold is then incubated (for example, at 37° C.) while polymerization of the elastin material is allowed to proceed, advantageously, for from between 15 minutes to 1 hour, 30 minutes being preferred. The reaction can be carried out at temperatures less than 37° C., but the reaction proceeds more rapidly at 77° C. Heating the reaction to over 40° C., however, can result in denaturation of the thrombin. Cooling of the mixture while stirring allows more time for mixing to occur. For polymerization to occur, it is important to have calcium and magnesium in the buffer.

Following polymerization in the mold, the resulting biomaterial can be further cross-linked using gamma radiation or an agent such as glutaraldehyde (a solution of glutaraldehyde, formic acid and picric acid being preferred). When radiation is used, the samples are, advantageously, subjected to gamma-irradiation from a Cobalt-60 source. The amount of irradiation can range, for example, from 10 to 100 MRAD, with 25 MRAD being preferred. It has been shown that the amount of gamma-irradiation can affect the strength of the material (Aprahamian, J.Biomed. Mat. Res. 21:965 (1987).

Sheets of biomaterial can be prepared that are of a controlled thicknesses by using appropriate molds. Sheets of the biomaterial can be made in thicknesses ranging, for example, from 200 microns to 5 mm. By way of example, a sheet suitable for use as an intestinal patch can range in thickness from 200 microns to 5 mm, with about 2 mm being preferred. A patch requiring greater strength is typically thicker.

As indicated above, biomaterial suitable for use in the present invention can be prepared from digests of tissue containing an elastin matrix. Tissues suitable for use as a starting material include arteries (e.g. coronary or femoral arteries, for example, from swine), umbilical cords, intestines, ureters, etc. Preferably, the matrix material is (derived from the species of animal in which the implantation is being performed so that bio-compatibility is increased. Any method of removing (digesting away) cellular material, proteins and fats from the native matrix while leaving the extracellular elastin matrix intact can be used. These methods can involve a combination of acidic, basic, detergent, enzymatic, thermal or erosive means, as well as the use of organic solvents. This may include-incubation in solutions of sodium hydroxide, formic -acid, trypsin, guanidine, ethanol, diethylether, -acetone, t-butanol, and sonication. Typically, the digestion proceeds more quickly at higher temperatures. The optimal temperature and time of incubation depend on the starting material and digestive agent used and can be readily determined.

The biomaterial of the invention, whether prepared from elastin powder or from tissues digests, is normally secured to existing tissue. When necessary, a small number of surgical sutures (eg stay sutures) can be used to appose the edges of the vessel together or to sew the vessel.

EXAMPLE 1

A mortal duodenal injury was created and repaired in six domestic swine.

The repair was performed with a bilaminar elastin patch, a cyanoacrylate adhesive, and a four stay sutures. After 4 to 6 weeks the animals were sacrificed and the specimens harvested. The repair was successful with all of the animals having normal weight gain during the experiment.

Figure 2:
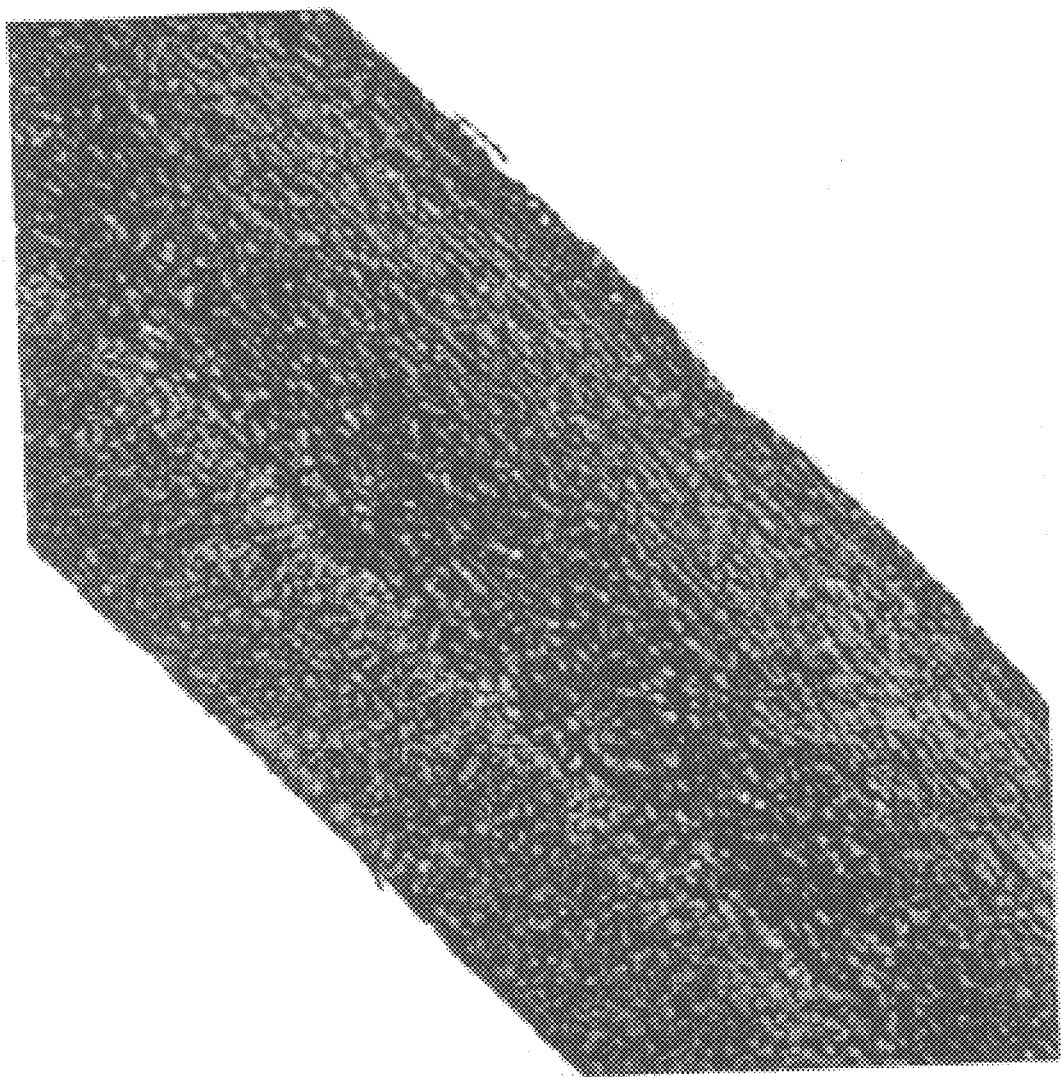
FIG. 2: Verhoeffs van Gleson stain of a cross-section of an elastin patch

The elastin bilaminar patch was made from porcine aortic tissue. Each porcine aorta was immersed in 80% ethanol for 72 hours and then digested in NaOH to remove everything except the elastin. This aortic elastin was then cut into 4×4 cm patches and pressed together orthogonally under approximately 50 psi. The result was a cross-oriented bilaminar patch as shown in FIGS. 1 and 2. After preparation the patches were sterilized in the autoclave.

An absorbable cyanoacrylate based tissue adhesive, developed and manufactured by PolyMed, Inc. of Anderson, S.C., was used to adhere and seal the elastin bilaminar patch to the duodenum. The adhesive was PolyMed GF-62 which comprises 95% by weight of methoxypropyl cyanoacrylate and 5% by weight of a solid miscible polymeric component comprising a copolymer of caprolactone and glycolide.

Figure 3:
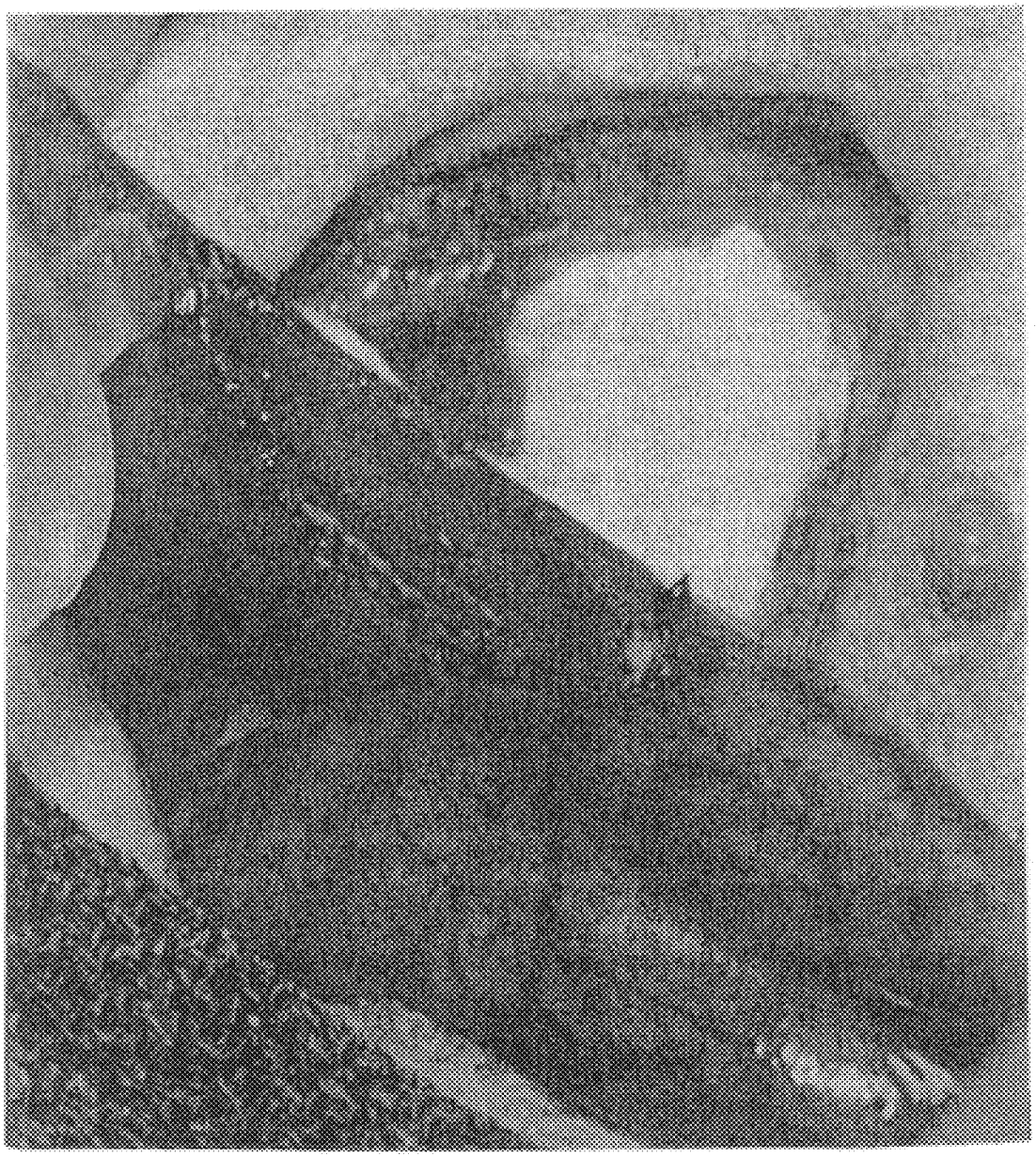
FIG. 3: Defect in duodenum

Six domestic swine were anesthetized and underwent cellotomy. The second portion o the duodenum was exposed. A Grade III circular defect 2 cm in diameter, was excised, which resulted in the removal of approximately 50% of the circumference of the duodenum at that location. A circular patch 3 cm in diameter was cut out of the elastin bilaminar patch. The tissue adhesive was applied around the edges of the defect with a syringe (FIG. 3). The patch was applied and held in place for approximately three minutes.

Figure 4:
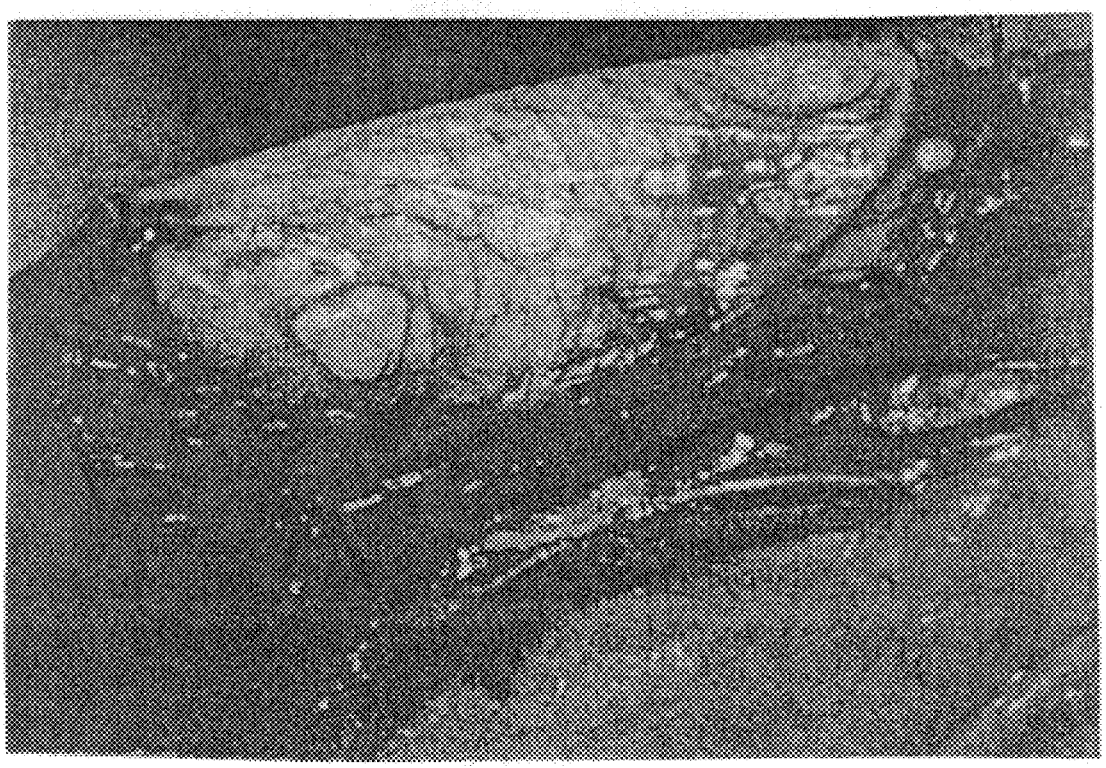
FIG. 4: Completed repair of duodenum with omental covering.

Six interrupted stay sutures were placed to anchor the patch in position. The entire patch area was wrapped with the omentum (FIG. 4). The animal was allowed to resume normal feeding within the first hour after extubation. No antibiotics or antacids were given post-operatively. The swine were sacrificed at 4 or 6 weeks after inplantation. The repaired duodenum was excised and sent for histological analysis, including Movat, H&E, and von Kossa staining.

Elastin patches were quickly deployed and the duodenum successfully sealed and repaired in all 6 animals. In most cases the entire surgery was performed in 30 minutes. The feeding habits and weight gain of the animals were normal. One pig was sacrificed at 4 weeks and the rest at 6 weeks. No duodenal or pancreatic fistulae were observed.

Figure 5:
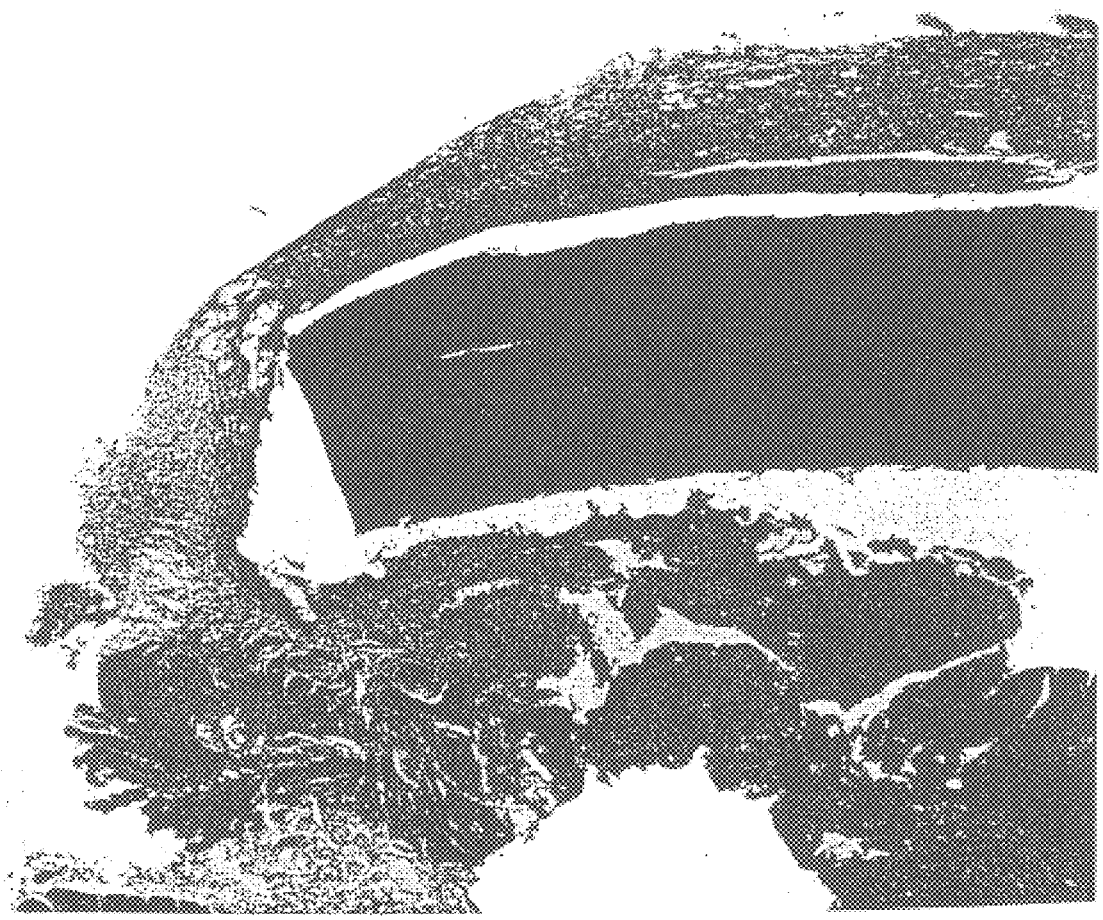
FIG. 5: Movat stain of 4 week patch.
Figure 6A:
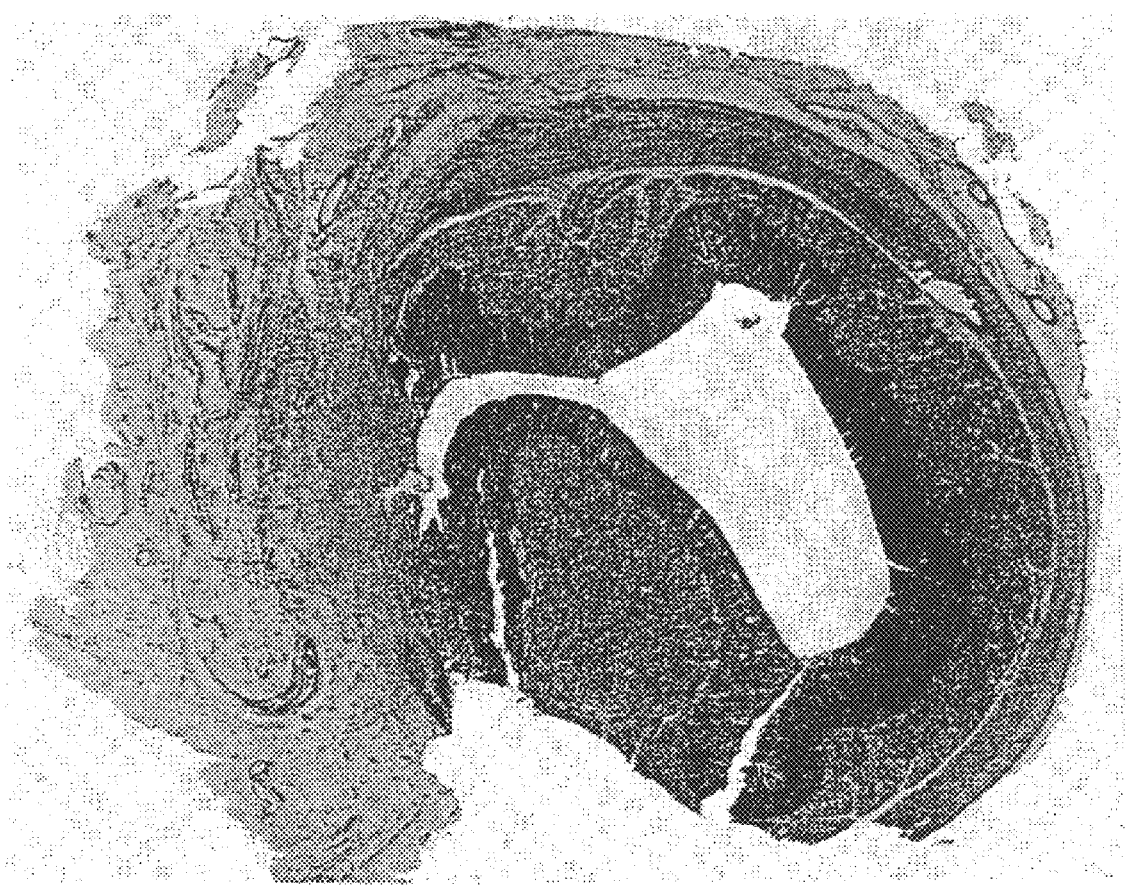
FIG. 6A: A Movat of haled duodendum at 6 weeks.
Figure 6B:
FIG. 6B: Section of injured site with mucosal cells on the right and pieces of elastin on the left (arrows).

Histological analysis at 4 weeks showed that the portion of elastin patch exposed to the duodenal contents was frayed and being degraded. The non-exposed end of the patch had fibrotic scar tissue surrounding it (FIG. 5). Little of the original elastin patch remained in the six week animals (FIG. 6A). Some elastin fibers were being extruded into the lumens, while some smaller pieces were being digested by inflammatory cells. In general, the wound was covered with inflammatory cells at the lumen scar tissue in the middle with pieces of remaining elastin, and omentum tissue on the outside (FIG. 6B). The wound was healing by contraction with evidence of mucosal tissue at the wound edges.

The elastin patch had, at a pH of 4.4, a Shrear Strength (24 hour) of 17 kPa, a Shear Strength (7 day) of 11 kPa, a Flexibility of 6523kPa, was bilaminar, and formed a water-tight and air tight seal when joined to a tissue substrate.

EXAMPLE 2

The procedure of EXAMPLE 1 was repeated except that was PolyMed 89B. The elastin patch produced at a pH of 4.4 had a Shrear Strength (24 hour) of 17 kPa, a Shear Strength (7 day) of 10 kPa, was bilaminar, and formed a water-tight and air tight seal when joined to a tissue substrate.

Thus, in EXAMPLES 1 & 2 the elastin patch secured with a biocompatible adhesive successfully covered the large defect in the duodenum, effecting tissue replacement, and preventing leakage of gastrointestinal contents into the abdominal cavity without causing subsequent infection. The elastin patch of this invention, and the method of applying same to the tissue substrate, allowed a simple, rapid repair for a difficult injury.

What is claimed is:

1. A method for producing an adherable biomaterial patch which can be joined onto a tissue substrate, comprising:
providing a biomaterial patch consisting essentially of elastin or an elastin-based biomaterial having at least one outer surface; and
treating the at least one outer surface of the biomaterial patch with a cyanoacrylate adhesive to produce said adherable biomaterial patch.

2. The method of claim 1, wherein said adherable biomaterial patch can be joined onto a tissue substrate in a highly acidic environment.

3. The method of claim 1, wherein said adherable biomaterial patch has a minimum hold time of at least about 48 hours.

4. The method of claim 1, wherein the pH in a highly acidic environment is not more than about 5.5 during at least a portion of said minimum hold time.

5. The method of claim 1, wherein said tissue substrate is a gastrointestinal system or a portion thereof.

6. The method of claim 1, wherein said adherable biomaterial patch has a 24 hour shear strength of at least about 10 kPa.

7. The method of claim 1, wherein said adherable biomaterial patch has a 7 day shear strength of at least about 10 kPa.

8. The method of claim 1, wherein said adherable biomaterial patch has a minimum cure time of at not more than about 3 minutes.

9. The method of claim 1, wherein said adherable biomaterial patch has a flexibility of at least about 100 kPa.

10. The method of claim 1, wherein said cyanoacrylate adhesive comprises an alkoxyalkyl cyanoacrylate.

11. The method of claim 1, wherein the cyanoacrylate adhesive comprises from an methoxypropyl cyanoacrylate.

12. The method of claim 1, wherein the cyanoacrylate adhesive further includes an additive comprising caprolactone.

13. The method of claim 1, wherein the cyanoacrylate adhesive further includes an additive comprising a copolymer of caprolactone and glycolide.

14. The method of claim 1, wherein the tissue substrate comprises all or a portion of the gastrointestinal system, the pulmonary system, and the vascular system.

15. The method of claim 1, wherein the biomaterial patch is bilaminar.

16. The method of claim 1, wherein adherable biomaterial patch is joined onto a tissue substrate to form a substantially water-tight seal.

17. The method of claim 1, wherein adherable biomaterial patch is joined onto a tissue substrate to form a substantially air-tight seal.

18. An adherable biomaterial patch which can be joined onto a tissue substrate, comprising:
a biomaterial patch consisting essentially of elastin or an elastin-based biomaterial having at least one outer surface; and
a cyanoacrylate adhesive applied onto at least one outer surface of the biomaterial patch.

19. The patch of claim 18, wherein said adherable biomaterial patch can be joined onto a tissue substrate in a highly acidic environment.

20. The patch of claim 18, wherein said adherable biomaterial patch has a minimum hold time of at least about 48 hours.

21. The patch of claim 18, wherein the pH in a highly acidic environment is not more than about 5.5 during at least a portion of said minimum hold time.

22. The patch of claim 21, wherein said tissue substrate is a gastrointestinal system or a portion thereof.

23. The patch of claim 18, wherein said adherable biomaterial patch has a 24 hour shear strength of at least about 10 kPa.

24. The patch of claim 18, wherein said adherable biomaterial patch has a 7 day shear strength of at least about 10 kPa.

25. The patch of claim 18, wherein said adherable biomaterial patch has a minimum cure time of at not more than about 3 minutes.

26. The patch of claim 18, wherein said adherable biomaterial patch has a flexibility of at least about 100 kPa.

27. The patch of claim 18, wherein said cyanoacrylate adhesive comprises an alkoxyalkyl cyanoacrylate.

28. The patch of claim 18, wherein the cyanoacrylate adhesive comprises from an methoxypropyl cyanoacrylate.

29. The patch of claim 18, wherein the cyanoacrylate adhesive further includes an additive comprising caprolactone.

30. The patch of claim 18, wherein the cyanoacrylate adhesive further includes an additive comprising a copolymer of caprolactone and glycolide.

31. The patch of claim 18, wherein the tissue substrate comprises all or a portion of the gastrointestinal system, the pulmonary system, and the vascular system.

32. The patch of claim 18, wherein the biomaterial patch is bilaminar.

33. The patch of claim 18, wherein adherable biomaterial patch is joined onto a tissue substrate to form a substantially water-tight seal.

34. The patch of claim 18, wherein adherable biomaterial patch is joined onto a tissue substrate to form a substantially air-tight seal.

35. A method for producing an adherable biomaterial patch which is joined onto a tissue substrate in a highly acidic environment, comprising:

provides a biomaterial patch consisting essentially of elastin or an elastin-based biomaterial having at least one outer surface;

treating the at least one outer surface of the biomaterial patch with a cyanoacrylate adhesive to produce said adherable biomaterial patch; and adhering said adherable biomaterial patch onto said tissue substrate.

36. The method of claim 35, wherein said adherable biomaterial patch can be joined onto a tissue substrate in a highly acidic environment.

37. The method of claim 35, wherein said adherable biomaterial patch has a minimum hold time of at least about 48 hours.

38. The method of claim 35, wherein the pH in a highly acidic environment is not more than about 5.5 during at least a portion of said minimum hold time.

39. The method of claim 35, wherein said tissue substrate is a gastrointestinal system or a portion thereof.

40. The method of claim 35, wherein said adherable biomaterial patch has a 24 hour shear strength of at least about 10 kPa.

41. The method of claim 35, wherein said adherable biomaterial patch has a 7 day shear strength of at least about 10 kPa.

42. The method of claim 35, wherein said adherable biomaterial patch has a minimum cure time of at not more than about 3 minutes.

43. The method of claim 35, wherein said adherable biomaterial patch has a flexibility of at least about 100 kPa.

44. The method of claim 35, wherein said cyanoacrylate adhesive comprises an alkoxyalkyl cyanoacrylate.

45. The method of claim 35, wherein the cyanoacrylate adhesive comprises from an methoxypropyl cyanoacrylate.

46. The method of claim 35, wherein the cyanoacrylate adhesive further includes an additive comprising caprolactone.

47. The method of claim 35, wherein the cyanoacrylate adhesive further includes an additive comprising a copolymer of caprolactone and glycolide.

48. The method of claim 35, wherein the tissue substrate comprises all or a portion of the gastrointestinal system, the pulmonary system, and the vascular system.

49. The method of claim 35, wherein the biomaterial patch is bilaminar.

50. The method of claim 35, wherein adherable biomaterial patch is joined onto a tissue substrate to form a substantially water-tight seal.

51. The method of claim 35, wherein adherable biomaterial patch is joined onto a tissue substrate to form a substantially air-tight seal.

* * * * *